(12) United States Patent
Iida et al.

(10) Patent No.: US 9,668,958 B2
(45) Date of Patent: Jun. 6, 2017

(54) NONCARIOUS MATERIAL AND ANTICARIOUS AGENT CONTAINING RARE SUGAR

(75) Inventors: Tetsuo Iida, Itami (JP); Takashi Ichihara, Itami (JP); Ken Izumori, Kagawa (JP); Masaaki Tokuda, Kagawa (JP); Takaaki Ogawa, Kagawa (JP)

(73) Assignees: MATSUTANI CHEMICAL INDUSTRY CO., LTD., Hyogo (JP); NATIONAL UNIVERSITY CORPORATION KAGAWA UNIVERSITY, Kagawa (JP)

(*) Notice: Subject to any disclaimer, the term of this patent is extended or adjusted under 35 U.S.C. 154(b) by 0 days.

(21) Appl. No.: 13/369,780

(22) Filed: Feb. 9, 2012

(65) Prior Publication Data

US 2013/0344008 A1 Dec. 26, 2013

Related U.S. Application Data

(62) Division of application No. 12/514,182, filed as application No. PCT/JP2007/056449 on Mar. 27, 2007, now Pat. No. 8,496,915.

(30) Foreign Application Priority Data

Nov. 10, 2006 (JP) ................................ 2006-305817

(51) Int. Cl.
| | | |
|---|---|---|
| A61K 8/60 | (2006.01) | |
| A61Q 11/00 | (2006.01) | |
| A61K 31/047 | (2006.01) | |
| A61K 31/7004 | (2006.01) | |
| C07H 3/02 | (2006.01) | |

(52) U.S. Cl.
CPC .............. *A61K 8/60* (2013.01); *A61K 31/047* (2013.01); *A61K 31/7004* (2013.01); *A61Q 11/00* (2013.01); *C07H 3/02* (2013.01)

(58) Field of Classification Search
None
See application file for complete search history.

(56) References Cited

U.S. PATENT DOCUMENTS

| 4,134,999 | A | | 1/1979 | Muhler et al. |
|---|---|---|---|---|
| 4,906,480 | A | | 3/1990 | Kashket |
| RE33,719 | E | * | 10/1991 | Levin .......................... 426/658 |
| 5,204,089 | A | * | 4/1993 | Hara et al. ...................... 424/58 |
| 5,811,271 | A | | 9/1998 | Izumori et al. |
| 2002/0086067 | A1 | | 7/2002 | Choi et al. |
| 2003/0019312 | A1 | | 1/2003 | Gumpoltsberger et al. |
| 2005/0002880 | A1 | | 1/2005 | Mummert et al. |
| 2005/0245459 | A1 | | 11/2005 | Izumori et al. |
| 2006/0210697 | A1 | | 9/2006 | Mower |
| 2007/0116831 | A1 | * | 5/2007 | Prakash et al. ................ 426/548 |

FOREIGN PATENT DOCUMENTS

| AU | 2003235403 A1 | | 12/2003 |
|---|---|---|---|
| EP | 415126 A1 | * | 3/1991 |
| WO | 96/16633 A1 | | 6/1996 |
| WO | WO 9616633 A1 | * | 6/1996 |
| WO | 03/097820 A1 | | 11/2003 |

OTHER PUBLICATIONS

K.S. Devulapalle and G. Mooser. Subsite Specificity of the Active Site of Glucosyltransferases from *Streptococcus sobrinus*. The Journal of Biological Chemistry. vol. 269, No. 16, Issue of Apr. 22, pp. 11967-11971, 1994.*

Hara, Y. "Prophylactic Functions of Tea Catechins", Chapter 3 of Protective Effects of Tea on Human Health, edited by Jain, N. K. et al. Cambridge MA: CABI North America, 2006, p. 18.*

Angela J. Yoon, Jing Shen, Regina M. Santella, Elizabeth M. Philipone, Hui-Chen Wu, Sidney B. Eisig, Andrew Blitzer, Lanny G. Close, and David J. Zegarelli. Topical Application of Green Tea Polyphenol (−)-Epigallocatechin-3-gallate (EGCG) for Prevention of Recurrent Oral Neoplastic Lesions. J Orfac Sci. 2012 ; 4(10): 43-50.*

T. Yamamoto, L R Juneja, D-C Chu, and M Kim. Chemistry and Applications of Green Tea. Boca Raton, FL: CRC Press, 1997, pp. 89-90.*

S. Mohri, K. Tokuori, Y. Endo, K. Fujimoto. Prooxidant activities in fish skin extractes and effects of some antioxidants and inhibitors on their activities. Fisheries Science 65(2), 269-273 (1999).*

AJ Yoon, J Shen, RM Santella, EM Pilipone, H-C Wu, SB Eisig, A Blitzer, LG Close, DJ Zegarelli. Topical application of green tea polyphenol (−)-epigallocatechin-3-gallate (EGCG) for prevention of recurrent oral neoplastic lesions. J Orofac Sci. 2012, 4(10), 43-50.*

Oh, D. K., "Tagatose: properties, applications, and biotechnological processes", Appl. Microbiol. Biotechnol, 2007, pp. 1-8, vol. 76.

Oshima, H. et al., "Psicose Contents in Various Food Products and Its Origin", Food Sci. Technol. Res., 2006, pp. 137-143, vol. 12, No. 2.

Hough, L. et al., "Variation of the allitol content of ITEA plants during photosynthesis", Phytochemistry, 1966, pp. 171-175, vol. 5.

Bar, A., Expert Panel Consensus Statement the Generally Recognized as Safe (GRAS) Status for D-Tagatose, Apr. 2, 2000, Supplied in four PDF documents.

Hamilton-Miller, J.M.T., "Anti-cariogenic properties of tea (Camellia sinensis), J. Med. Microbiol" 2001, pp. 299-302, vol. 50.

(Continued)

*Primary Examiner* — Frederick Krass
*Assistant Examiner* — Michael P Cohen
(74) *Attorney, Agent, or Firm* — Westerman, Hattori, Daniels & Adrian, LLP

(57) ABSTRACT

To provide a composition for preventing periodontal diseases (prophylactic agent of periodontal diseases), the composition having an excellent cariostatic property, being safe and stable for prolonged use and having less effects on flavor. A non-cariogenic material prepared by blending a rare sugar in the D form as selected from the group consisting of D-psicose, D-sorbose and D-tagatose, a rare sugar in the L form as selected from L-fructose, L-psicose and L-tagatose, or allitol as a rare sugar derivative, singly or in combination. A cariostatic agent comprising D-psicose, D-sorbose, D-tagatose, L-fructose, L-psicose and/or L-tagatose. A cariostatic agent in combination with catechins.

1 Claim, 5 Drawing Sheets

(56) References Cited

OTHER PUBLICATIONS

Miura, Y. et al., "Tea Catechins Prevent the Development of Atherosclerosis in Apoprotein E-Deficient Mice", The Journal of Nutrition, 2001, pp. 27-32, No. 131.

* cited by examiner

NONCARIOUS MATERIAL AND ANTICARIOUS AGENT CONTAINING RARE SUGAR

CROSS-REFERENCE TO RELATED APPLICATIONS

This is a divisional application of U.S. patent application Ser. No. 12/514,182, filed on Jan. 15, 2010, currently pending, which is a 371 of International Application No. PCT/JP2007/056449, filed on Mar. 27, 2007, which claims the benefit of priority from the prior Japanese Patent Application No. 2006-305817, filed on Nov. 10, 2006, the entire contents of which are incorporated herein by references.

TECHNICAL FIELD

The present invention relates to a non-cariogenic material and a cariostatic agent, which contain rare sugars. More specifically, the invention relates to a composition comprising the non-cariogenic material in blend and a cariostatic composition comprising the cariostatic agent in blend.

BACKGROUND ART

Dental caries (terms "caries tooth, dental caries, and tooth caries, decayed teeth, etc." mean the same disease; thus, these terms are abbreviated as "caries" hereinafter) is a disease caused by oral bacteria generating acids using sugars, particularly sucrose as a nutritious source to cause decalcification of teeth with the acids (the solubilization of inorganic components phosphoric acid and calcium from dental enamel and dentine with acids) and then decay teeth.

Various theories have been proposed about the detailed etiology of caries. Currently, it is understood that caries is initiated by the deposition of an insoluble, adhesive polysaccharide (insoluble glucan) generated by *Streptococcus mutans* (sometimes abbreviated as "*S. mutans*" hereinafter) on the dental surface. Specifically, insoluble glucan is generated from sucrose by bacteria such as *Streptococcus mutans*; the insoluble glucan deposits on dental surface to form dental plaque by oral bacteria and with food residues. Various microorganisms mainly including *Streptococcus mutans* can concurrently exist and proliferate in the dental plaque. Through the metabolism of these microorganisms, acids are generated; with the action of the acids, the pH is reduced to cause dental decalcification, leading to tooth decay and additionally to cause the occurrence and progress of caries.

Because caries occur due to the causes described above, one of preferable prophylactic approaches therefor is no intake of sugars causing the generation of insoluble glucan and acids by oral bacteria, such as sucrose. Because sucrose is abundantly contained in the natural kingdom and agricultural products such as fruits and vegetables and is an indispensable item in seasonings and foods for our daily dietary life, it is very hard to achieve no sucrose intake.

In such circumstances, so far, alternative sugars such as Xylitol (patent reference 1, patent reference 2), Palatinit (patent reference 3) and erythritol (non-patent reference 1) have been developed. The effects thereof on the prevention of acid generation and dental plaque formation with caries-inducing bacteria have been elucidated. Additionally, D-arabitol at a sweetness level of about 68% of the sweetness level of sucrose, D-allose at a sweetness level of about 65% of the sweetness level of sucrose and L-mannose at the same sweetness level as that of glucose have been proposed as non-cariogenic materials (patent reference 4). Furthermore, the use of a cyclic tetrose D-psicose as a material inducing a low level of caries has also been suggested (patent reference 5).

Still further, it has been known commonly that dental plaque not only causes decayed teeth but also causes periodontal diseases such as gingivitis and periodontitis (gumboil). Therefore, it is an important issue to suppress or kill etiologic bacteria causing caries or periodontal diseases, such as *Streptococcus mutans*, so as to prevent such various diseases. Accordingly, oral compositions with such effects have been desired strongly. So as to apply such compositions to the prophylaxis and therapeutic treatment of periodontal diseases, the alternative sugars disadvantageously have problematic safety profiles when used in the oral compositions; the alternative sugars are hardly blended in stable manners in such oral compositions; the alternative sugars disadvantageously affect flavor; the alternative sugars have insufficient effects; and the cost for blending the alternative sugars therein is problematic.

Patent reference 1: JP-A-2000-128752
Patent reference 2: JP-A-2000-53549
Patent reference 3: JP-A-2000-281550
Patent reference 4: JP-A-2000-68970
Patent reference 5: WO 01-090338
Non-patent reference 1: Kawanabe et al., Caries Res. 26 p. 358-362 (1992)

DISCLOSURE OF THE INVENTION

Problems that the Invention is to Solve

Xylitol is a sugar alcohol belonging to rare sugars and has conventionally been added to favorite foods and foods, for use. It has been known commonly that Xylitol has a high effect on the prophylaxis of caries. It is surely understood that sugar alcohols such as Xylitol, Palatinit and erythritol hardly function as substrates for the glucan synthase generated by *Streptococcus mutans* and never serve as raw materials for water-soluble and water-insoluble glucan.

Furthermore, it has been indicated that Xylitol has such non-cariogenicity that Xylitol is never utilized by the group *Streptococcus mutans* and additionally that Xylitol exerts an action to promote the sterilization action against the group *Streptococcus mutans* and also exerts a recalcification-promoting action. By recent research works, meanwhile, it has been verified that because the group *Streptococcus mutans* cannot utilize Xylitol as energy, the proliferation and activity of *Streptococcus mutans* is reduced. In other words, the replacement of a part of sucrose in a sweetener with Xylitol leads to the reduction of the sucrose amount. In such manner, an effect of preventing caries can be obtained. It has been known that conventionally known sugar alcohols with a non-cariogenic action induce for example diarrhea at excess intake thereof and that the use of such sugar alcohols as alternative sugars of glucose and fructose is not appropriate because of the difference in physical properties. Thus, it has been desired the development of a novel non-cariogenic material durable on multiple uses as an alternative sugar.

Specifically, the development of a non-cariogenic material durable on multiple uses as alternative sugars of glucose and sucrose as major caloric sources and as important sweeteners as well as a caries-preventing sweetener containing the same has been desired. It has been expected to find a rare sugar with an effect as an anticarius sweetener among other rare sugars to create a novel "anticarius sweetener" using the same.

In accordance with the invention, it was found a novel non-cariogenic rare sugar with a property that the rare sugar is never metabolized with a bacterium causing caries, namely *Streptococcus mutans*, i.e. with a property involving no substantial generation of insoluble glucan or acids. Thus, it is an object of the invention to provide a non-cariogenic material in blend with the non-cariogenic rare sugar and a composition containing the same (anticarius sweetener).

In accordance with the invention, a novel cariostatic rare sugar was found, which had a property substantially suppressing acidification via the metabolism with caries-causing bacteria, when existed concurrently with a cariogenic sweetness ingredients to be metabolized with *Streptococcus mutans* as a caries-causing bacterium. Thus, it is an object of the invention to provide a cariostatic agent comprising the cariostatic rare sugar as well as a cariostatic composition prepared by blending the cariostatic agent.

It is an object of the invention to provide a composition for preventing periodontal diseases (prophylactic agent of periodontal diseases), the composition having excellent cariostatic properties, being safe and stable for a long period of use, and having less effects on flavor.

Means for Solving the Problems

The inventor made investigations so as to solve the problems. Consequently, the inventor found that a rare sugar in the D form as selected from the group consisting of D-psicose, D-sorbose and D-tagatose as rare sugars, a rare sugar in the L form as selected from the group consisting of L-fructose, L-psicose and L-tagatose or allitol as a rare sugar derivative cannot be assimilated by *Streptococcus mutans*, so that such rare sugar or rare sugar derivative suppresses the proliferation of *Streptococcus mutans*, never leading to pH reduction. Thus, the invention relating to a non-cariogenic material has been achieved. Additionally, the inventor found that D-psicose never causes pH reduction (i.e., D-psicose has a cariostatic property) even in the presence of sucrose as an assimilable sugar. The inventor additionally found that the cariostatic property could be enhanced with a combination with catechin. Thus, the invention relating to the cariostatic agent has been achieved.

The gist of the invention resides in the non-cariogenic material described below in (1).
(1) A non-cariogenic material prepared by blending a rare sugar in the D form as selected from the group consisting of D-psicose, D-sorbose and D-tagatose as rare sugars, a rare sugar in the L form as selected from the group consisting of L-fructose, L-psicose and L-tagatose or allitol as a rare sugar derivative, singly or in combination.

The gist of the invention resides in the composition described below in (2) through (7).
(2) A composition containing the non-cariogenic material described in (1).
(3) The composition described in (2), where the composition is a food composition.
(4) The composition described in (3), where the food composition is a food composition with a label telling the use thereof for preventing periodontal diseases.
(5) The composition described in (2), where the composition is an oral composition.
(6) The composition described in (5), where the oral composition is an oral composition with a label telling the use thereof for preventing periodontal diseases.
(7) The composition described in (2), where the composition is a pharmaceutical product or a quasi-pharmaceutical product, or a cosmetic product.
(8) The composition described in (7), where the pharmaceutical product or quasi-pharmaceutical product is a pharmaceutical product or quasi-pharmaceutical product to be used for preventing periodontal diseases.

The gist of the invention resides in a cariostatic agent described below in (9) or (10).
(9) A cariostatic agent comprising a rare sugar in the D form as selected from the group consisting of D-psicose, D-sorbose and D-tagatose as rare sugars, a rare sugar in the L form as selected from the group consisting of L-fructose, L-psicose and L-tagatose or allitol as a rare sugar derivative.
(10) The cariostatic agent described in (9), comprising catechins in combination.

The gist of the invention resides in a cariostatic oral composition described below in (11) or (12).
(11) A cariostatic oral composition prepared by blending the cariostatic agent described in (9) or (10).
(12) The cariostatic oral composition described in (11), where the cariostatic oral composition is a cariostatic oral composition with a label telling the use thereof for preventing periodontal diseases.

The gist of the invention resides in a cariostatic food composition described below in (13) or (14).
(13) A cariostatic food composition prepared by blending the cariostatic agent described in (9) or (10).
(14) The cariostatic pharmaceutical product, quasi-pharmaceutical product or cosmetic composition described in (13), where the cariostatic food composition is a food composition with a label telling the use thereof for preventing periodontal diseases.

The gist of the invention resides in a cariostatic pharmaceutical product or quasi-pharmaceutical product or a cosmetic composition described below in (15) or (16).
(15) A cariostatic pharmaceutical product or quasi-pharmaceutical product or a cosmetic composition prepared by blending the cariostatic agent described in (9) or (10).
(16) A cariostatic pharmaceutical product or quasi-pharmaceutical product or a cosmetic composition described in (15), where the cariostatic pharmaceutical product or quasi-pharmaceutical product is a pharmaceutical product or quasi-pharmaceutical product with a label telling the use thereof for preventing periodontal diseases.

Advantages of the Invention

In accordance with the invention, a non-cariogenic material can be provided, which is prepared by blending a rare sugar in the D form as selected from the group consisting of D-psicose, D-sorbose and D-tagatose as rare sugars, a rare sugar in the L form as selected from the group consisting of L-fructose, L-psicose and L-tagatose or allitol as a rare sugar derivative, singly or in combination, which is never metabolized with *Streptococcus mutans* and which never substantially causes the acidification of dental surface via acid generation. Additionally, various compositions containing the non-cariogenic material, such as food compositions, oral compositions, pharmaceutical products or quasi-pharmaceutical products, and cosmetics products can be provided.

Specifically, the non-cariogenic material of the invention can be blended in various compositions including foods, drinks, feeds, pharmaceutical products, quasi-pharmaceutical products and cosmetic products, as an alternative sweetener of conventional sweetness ingredients comprising sugars such as glucose, fructose, lactose and sucrose and various reduced sugar types, or as a replacement of at least a part of the conventional sweetness ingredients or in addition to the conventional sweetness ingredients. In case that the non-cariogenic material of the invention is contained in for example compositions such as foods or drinks, the risk of affliction with caries is reduced even if the foods or drinks are ingested. In case that all the sweetness ingredients in entirety are substantially composed of the non-cariogenic material of the invention, no possibility of caries affliction exists even through the intake, so that the compositions can be prepared as non-cariogenic food compositions or drinks. In accordance with the invention, further, an oral composition in blend with the rare sugars with a safety profile for humans and great stability can be provided, so that it can be expected that the oral composition of the invention exerts the effect of preventing periodontal diseases, via the blending of the rare sugars.

In case of the concurrent existence with cariogenic sweetness ingredients metabolizable with *Streptococcus mutans* as a bacterium causing caries in accordance with the invention, a cariostatic agent comprising cariostatic rare sugars with properties of substantially suppressing the acidification of dental surface through the metabolism of the bacterium causing caries, namely D-psicose, D-sorbose, D-tagatose, L-fructose, L-psicose and L-tagatose, and allitol or comprising the cariostatic rare sugars in combination with catechins can be provided. Additionally, cariostatic oral compositions, cariostatic food compositions, or cariostatic pharmaceutical products, quasi-pharmaceutical products or cosmetic compositions comprising the cariostatic agent in blend can be provided. More specifically, the cariostatic agent of the invention is added to products containing assimilable sugars such as glucose, fructose, lactose and sucrose and polyphenols such as catechin, to provide various cariostatic compositions such as oral compositions, food compositions, pharmaceutical products, quasi-pharmaceutical products or cosmetic products. In case that the cariostatic agent of the invention is blended in for example a food composition, it is understood that the risk of affliction with caries is at a level as low as possible even if the food composition is ingested. Even in case of the co-existence of a cariogenic sweetness ingredient with the sweetness ingredients, the possibility of affliction with caries is reduced even after the ingestion, so that the composition can be defined as a cariostatic food composition.

BEST MODE FOR CARRYING OUT THE INVENTION

In accordance with the invention, the term "non-cariogenicity" means a phenomenon or state substantially never causing the acidification of dental surface with acid generation since the non-cariogenic material per se is never metabolized with the bacterium causing caries, namely *Streptococcus mutans*.

Therefore, the term "non-cariogenicity" means the property that the non-cariogenic material per se is never metabolized with the bacterium causing caries so the non-cariogenic material never substantially causes the acidification of dental surface via acid generation. In other words, the property means a profile that as the consequence of culturing in a culture medium supplemented with 1 to 10% by weight of the rare sugars for 20 to 48 hours, the bacterial growth through the metabolism thereof is at a level identical to the bacterial growth level in case of no sugar addition (control) or at the given level or less; or the culture medium pH is at a level identical to the pH level in case of no sugar addition (control) or at the given level or less. The term "non-cariogenicity" means such property.

Additionally, the term "cariostatic" means a phenomenon or state substantially suppressing the acidification of dental surface via the metabolism with the bacterium causing caries, due to the co-existence of the cariostatic material with a cariogenic sweetness ingredient to be metabolized with the bacterium.

Thus, the term "cariostatic property" means a property that via the co-existence with a cariogenic sweetness ingredient to be metabolized with the bacterium, the acidification of dental surface via the metabolism with the bacterium causing caries can be suppressed substantially. Specifically, *Streptococcus mutans* was cultured in a culture medium supplemented with 1 to 10% by weight of the rare sugars in the co-existence of assimilable sugars. 20 to 48 hours later, the bacterial growth through the metabolism thereof is at the given level or less, compared with the bacterial growth level with no rare sugar addition (control); or the culture medium pH is at the given level or more, compared with no rare sugar addition (control). The term "cariostatic property" means the property described above.

In this specification, herein, the term "caries suppression" or "caries suppressing property" is used to mean both "non-cariogenicity" and "cariostaticity" in combination or "non-cariogenic property" and "cariostatic property" in combination, without any discrimination of these terms.

The "rare sugar" for use in accordance with the invention means a monosaccharide existing at a trace amount in the natural kingdom, while monosaccharides existing abundantly in the natural kingdom are defined as "natural monosaccharides".

Figure 4:
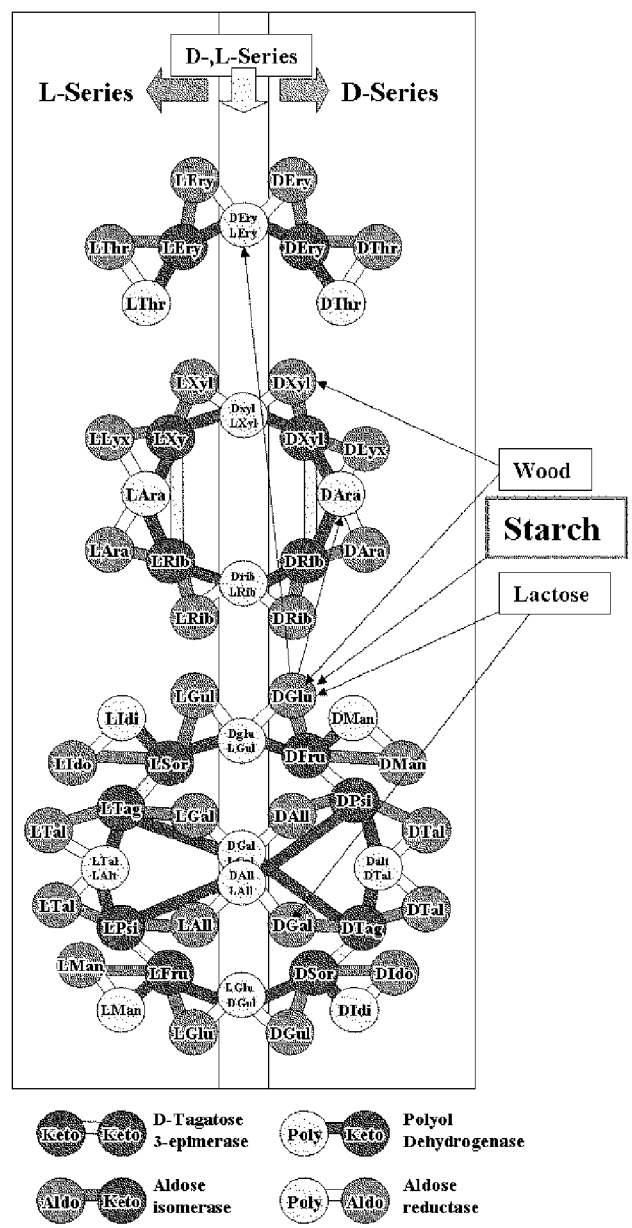
FIG. 4 Izumoring linking chart.

One of the inventors, Ken Izumori, publicly describes the Izumoring linking chart in the patent reference 1. Via the production processes and molecular structures (D- and L-forms) shown in FIG. 4, a linking chart where all monosaccharides with 4 to 6 carbon atoms (C) are linked together is the whole view of Izumoring. Those understandable in FIG. 4 are that all C4, C5 and C6 monosaccharides are linked together. The whole view shows the linking in Izumoring C6, the linking in Izumoring C5 and the linking in Izumoring C4, and the linking among all of C4, C5 and C6. This concept is very important. So as to reduce the number of carbon atoms, mainly, a fermentation method is used. Izumoring has a characteristic profile that all monosaccharides with different numbers of carbon atoms can be linked together in such a large linking chart.

Figure 5:
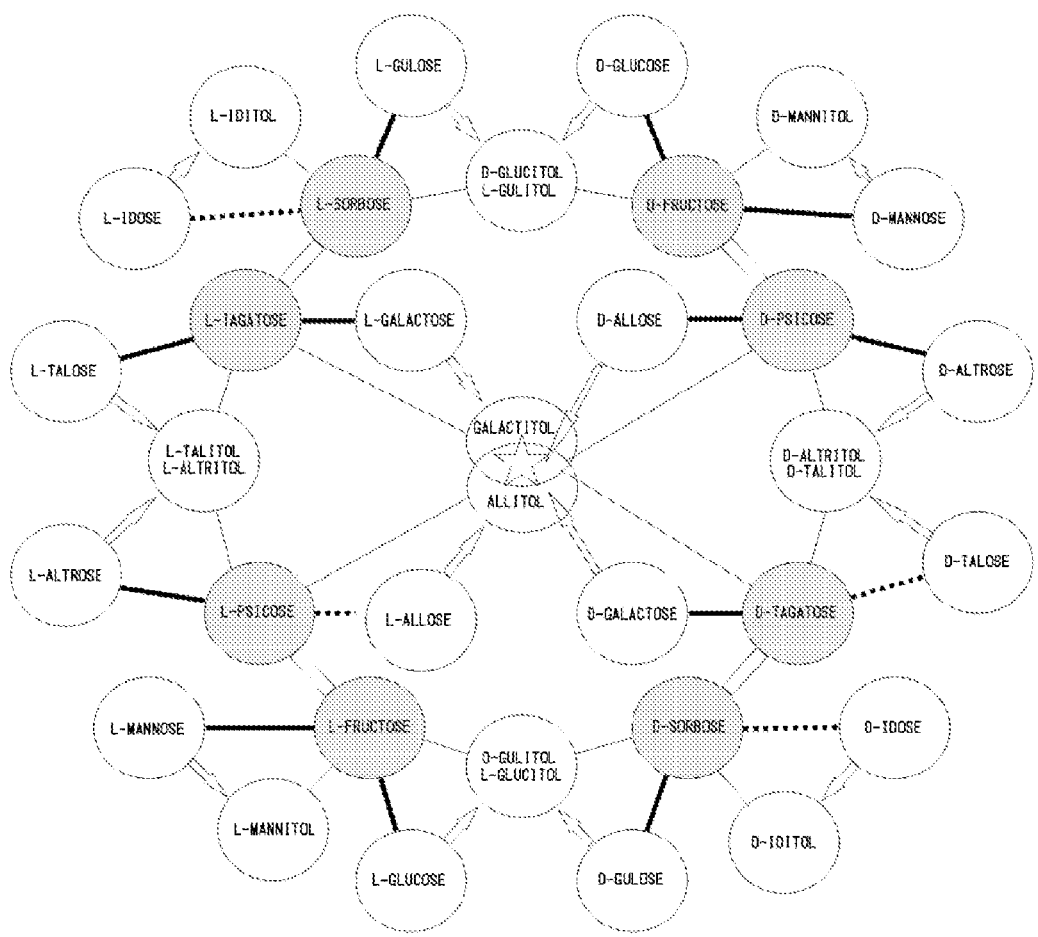
FIG. 5 Explanatory view of Izumoring C6 in the lower column of FIG. 4.
Figure 6:
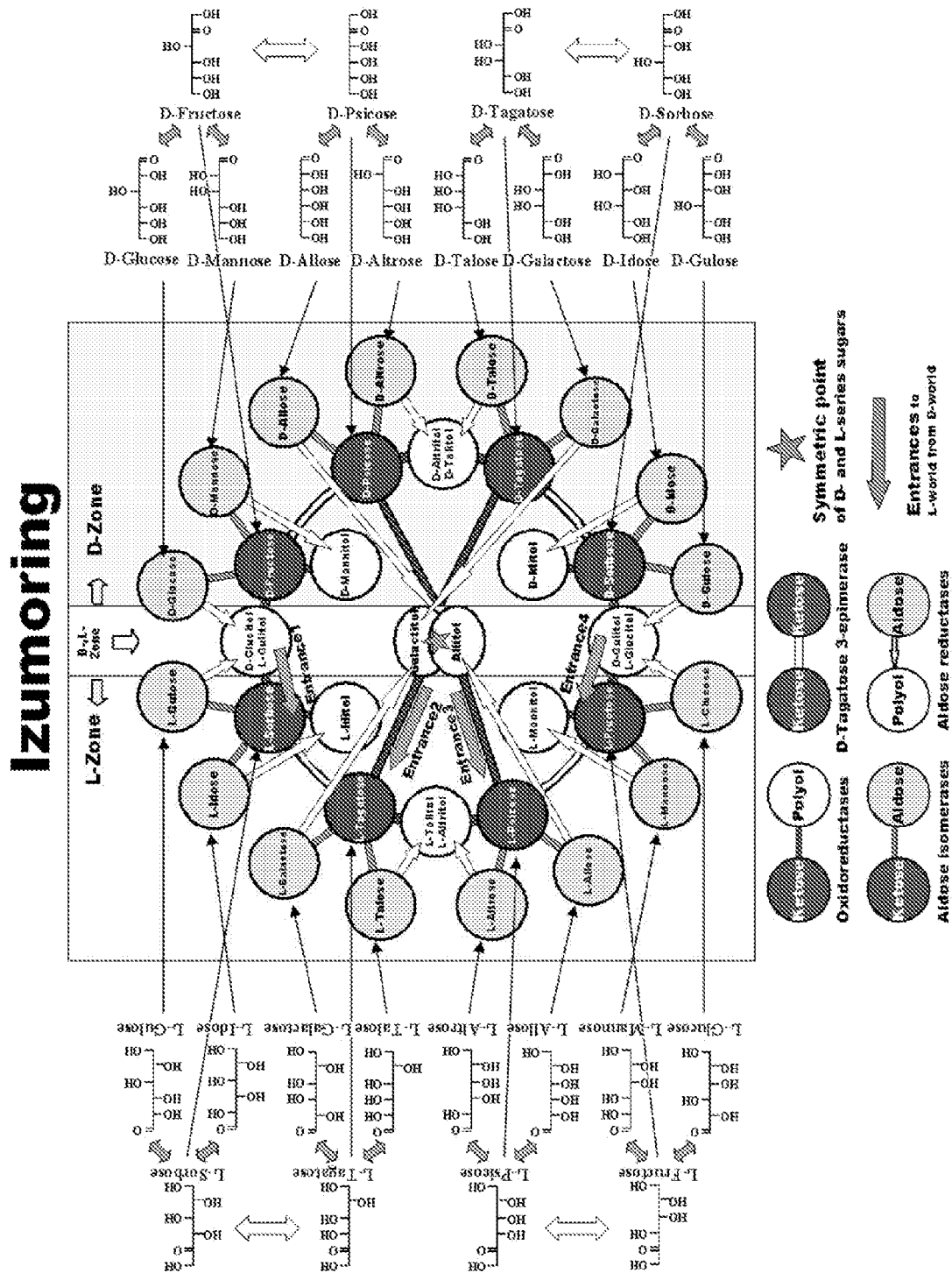
FIG. 6 Explanatory view of Izumoring C6 along with structural formulas.

According to Izumoring of monosaccharides with 6 carbon atoms (hexoses), as shown in the lower column of FIG. 4, and FIGS. 5 and 6, monosaccharides with 6 carbon atoms (hexoses) are in total of 34 types, where aldose includes 16 types; ketose includes 8 types and sugar alcohol includes 10 types. Rare sugars can be defined as monosaccharides rarely existing in the natural kingdom (aldose, ketose and sugar alcohol). Because the definition is not a definition based on the structure or properties of a sugar, the definition is quite ambiguous. In other words, no quantitative definition about the amount of a rare sugar at the given level or less is made. Generally, aldose abundantly existing in the natural kingdom includes for example D-glucose, D-galactose, D-mannose, D-ribose, D-xylose, and L-arabinose in total of 6 types; other aldoses are defined as rare sugars. Ketose abundantly existing is D-fructose; other ketoses are defined as rare sugars. Other ketoses include D-tagatose, D-sorbose, D-psicose, L-fructose, L-psicose, L-tagatose and L-sorbose. Additionally, sugar alcohols are prepared by reducing monosaccharides. In the natural kingdom, D-sorbitol relatively abundantly exists but other sugar alcohols are quantitatively less so it can be said that these sugar alcohols are also rare sugars.

It has been known from research works including the research works of the present inventors that these sugars can be converted by reactions with redox enzymes, reactions with aldose isomerase, and reactions with aldose reductases. In the research works so far, the group in the upper part of FIG. 2, the group in the middle part thereof and the group in the lower part thereof have not been linked together. Specifically, D-glucose (grape sugar) and D-fructose belonging to the upper group are sugars abundantly existing in the natural kingdom and are therefore inexpensive, but no rare sugars could have been prepared synthetically from these sugars. In the course of the research works of the inventors, an enzyme linking these sugars together was discovered. This is derived from the unexpected discovery of D-sorbose in a liquid culture of a bacterium with an enzyme synthetically preparing D-tagatose from galactitol. The cause was examined. Consequently, it was found that the bacterium generated the enzyme called D-tagatose 3-epimerase (DTE) (see for example JP-A-6-125776). As shown in the lower part of FIG. 4 and FIGS. 5 and 6, DTE is an enzyme linking together D-tagatose and D-sorbose, which have never been linked together so far. More surprisingly, then, it was indicated that DTE was an enzyme epimerizing all ketoses at position 3 and was a unique enzyme with wide varieties of substrate specificities interactive with D-fructose and D-psicose, L-sorbose and L-tagatose, D-tagatose and D-sorbose, and L-psicose and L-fructose. Via the discovery of DTE, all monosaccharides could be linked together in a ring shape, to complete the structural knowledge about monosaccharides. Then the ring was designated Izumoring.

When thoroughly examined, FIGS. 5 and 6 show that L forms are on the left side; D forms are on the right side; and DL forms are in the middle, where L forms and D forms are arranged in point symmetry, along the ring center (asterisk). For example, D-glucose and L-glucose are arranged in point symmetry on the central point as the basis. Additionally, Izumoring is valuable in that Izumoring is a design chart for producing all monosaccharides. When intending the production of L-glucose from D-glucose as the starting material, Izumoring shows that D-glucose is isomerized, epimerized, reduced, oxidized, epimerized and isomerized to prepare L-glucose.

Using Izumoring of monosaccharides with 6 carbon atoms (hexoses), the relation between sugars existing abundantly in the natural kingdom and rare sugars existing at trace amounts is shown. D-Glucose, D-fructose, D-mannose, and D-galactose producible from lactose in milk exist abundantly naturally, but other hexoses except those described above are rare sugars existing at trace amounts. Via the discovery of DTE, D-fructose and D-psicose could be produced from D-glucose; furthermore, D-allose, allitol and D-talitol could be produced. A rare sugar D-psicose has been hardly available so far. A method for producing rare sugars from monosaccharides abundantly existing naturally has been underway of development. D-Psicose can be produced using the technique therefor.

The significance of Izumoring about monosaccharides with 6 carbon atoms (hexoses) is now summarized. Depending on the production process and molecular structure (D form and L form), all monosaccharides can be structurally arranged (formation of structural knowledge), so that the whole image of monosaccharides can be grasped; and efficient and effective approaches for the research works can be selected; the optimal production route can be designed; and deficient parts can be projected.

In accordance with the invention, a rare sugar with the non-cariogenic property, which can be a non-cariogenic material, is a rare sugar in the D form as selected from the group consisting of D-psicose, D-sorbose and D-tagatose as rare sugars, a rare sugar in the L form as selected from the group consisting of L-fructose, L-psicose and L-tagatose or allitol as a rare sugar derivative. In accordance with the invention, further, rare sugars with cariostatic properties, which can be cariostatic agents, are D-psicose, D-sorbose, D-tagatose, L-fructose, L-psicose and/or L-tagatose.

Catechins for use in accordance with the invention are polyphenols contained in tea, and representatively include catechin and epicatechin with two hydroxyl groups in the ring B, epigallocatechin with three hydroxyl groups in the ring B, and epigallocatechin gallate with galloyl group. These catechins are described as active ingredients in compositions against periodontal diseases (U.S. Pat. No. 2,903,210). The effective catechin concentration against caries in the test system is 500 µg/ml, while the concentration of gallocatechin with the highest effectiveness is 125 µg/ml. Additionally, these catechins when polymerized together generate tannin, where the galloyl moiety has almost the same structure as that of gallic acid and pyrogallol. For the suppression of caries with these polyphenols, it is shown that a polyphenol with three hydroxyl groups is particularly effective and even a polyphenol with two hydroxyl groups is also effective (Tsutomu Okubo, Food Style 21, 8, p. 47-51 (2004)). Accordingly, it is understood that polyphenols with two hydroxyl groups, such as caffeic acid contained in coffee, would be effective against caries.

Because these substances are bitter ingredients with strong astringency, however, the resulting taste is significantly deteriorated, disadvantageously from the standpoint of applications thereof to various fields including foods. Examinations should be made about a compound exerting the antibacterial and caries-suppressing properties even when the amount of polyphenols used therein such as catechins is reduced so as to reduce the bitterness.

The non-cariogenic material or the cariostatic agent in accordance with the invention has a non-cariogenic function (action) of a rare sugar contained therein or a cariostatic function (action) of a rare sugar as the cariostatic agent and additionally has various functions (actions) and uses, for example hypoglycemic action and sweetness-giving action (sweetener). For example, D-psicose is at a sweetness level at about 70% of the sweetness level of sucrose and is substantially zero kilocalories (Matsuo et al., J. Nutr. Sci. Vitaminol. 48 pp. 77-80 (2002)), and is therefore useful as a low-calorie sweetener. Additionally, D-psicose may also be used as a thickener, a moistening agent, an excipient, a modifier of physical properties and a filler.

Therefore, the invention relates to various compositions containing the caries-suppressing material (non-cariogenic material or cariostatic agent). As an alternative sweetener of conventional sweetness ingredients comprising sugars such as glucose, fructose, lactose and sucrose and reduced various sugars or in place of at least a part thereof, or in addition to the conventional sweetness ingredients, the non-cariogenic material or cariostatic agent of the invention can be blended in various compositions, preferably at a concentration about 20-fold the concentration of assimilable sugars, so that the resulting compositions can exert the non-cariogenic function (action) or the cariostatic function (action). By allowing the various compositions to contain polyphenols such as catechin (at about 0.002% or more), the cariostatic function (action) can be enhanced. In other words, the inventive material can be blended less (about 10-fold the amount of assimilable sugars). Examples of the use of such compositions include foods (including drinks and feeds for animals), cosmetic products, pharmaceutical compositions and oral compositions. Pharmaceutical products and foods and drinks, for humans and animals, include for example modified milk powder, enteral nutritious agents, health foods and drinks, additives for feeds, and confectionaries. The pharmaceutical products and the foods and drinks should finally be in orally administrable forms, with no specific limitation. Oral compositions for humans and animals include those with conventionally known, appropriate uses, types and forms in the field.

When the caries-suppressing material is used as a food or drink (including food compositions with a label telling the use thereof for preventing periodontal diseases), the caries-suppressing material of the invention (caries-suppressing material containing any of the non-cariogenic material and the cariostatic material) or a processed product thereof may be used as it is or may be blended with other foods or food ingredients according to routine methods for use. The term "processed product" means a processed food containing the food and widely includes apparent foods (foods in the narrow sense) to tablets. For processing, general processing methods for foods may be applicable with no problem, owing to the high thermostability and the high acid stability. The composition of the invention may be in any form of powders, granules, pastes, liquids, and suspensions, with no specific limitation. The composition may be formulated into for example, health drinks and compositions in confectionary tablet forms, where sweeteners, sour agents, vitamins and other various ingredients for routine use in producing drinks are used.

The food composition includes for example appropriate known ones conventionally in the technical field, particularly food compositions with sweetness ingredients, for example drinks, chewing gum, chocolate and candy. Additionally, the food composition can get an enhanced cariostatic function (action) when the food composition contains phenolic compounds such as catechin. The caries-suppressing foods in accordance with the invention are preferably in any one of for example cake, cookies, chocolate, gum, sponge cake (pao de Castella), bread, ice cream, pudding, jelly, bavarois, cream, caramel, jam, bean jam, candies, bar of sweet jellied adzuki-bean paste, bean-jam-filled wafers and confectionaries. Additionally, the caries-suppressing drinks and foods in accordance with the invention are preferably in any of for example carbonate drinks, sour milk beverages, fruit juice drinks, and juice.

For providing the caries-suppressing material in the form of confectionaries such as chewing gum, candies, confectionary tablet, jelly and Gummi, raw material components including the caries-suppressing material of the invention are mixed together under agitation with a kneader, to produce such confectionaries. Additionally, sugar sweeteners such as various maltose and reduced glutinous starch syrup, Siraitia grosenorii extracts and sweeteners at high sweetness levels such as aspartame and stevioside, may also be used concurrently.

The content of the rare sugar is not specifically limited but is generally 0.1 to 99% in the composition so as to achieve the effect. The composition of the invention may additionally contain one or two or more of Xylitol, maltitol, Palatinit, mannitol, sorbitol, palatinose, panose oligosaccharide, lactitol, erythritol, coupling sugar and isomalto-oligo, which are considered to have caries induction-suppressing actions.

In case that the caries-suppressing material of the invention is contained in for example a composition as a food or a drink, it is understood that the risk of caries affliction may be reduced by the intake of the material. In case that the sweetness ingredients in the composition of a food or a drink substantially totally comprise the caries-suppressing material of the invention, the possibility of affliction with caries is substantially zero even when the composition is ingested. Hence, the composition can be said as a caries-suppressing food composition or drink.

In case that the caries-suppressing material of the invention is used as a pharmaceutical composition (including a composition for preventing periodontal diseases), the caries-suppressing material can be added to various pharmaceutical preparations. The pharmaceutical preparations include for example oral administration preparations such as tablets, capsules, granules, powders and syrups. In the caries-suppressing material of the invention, base materials are used as a part thereof. Additionally, these various pharmaceutical preparations can be prepared by using known auxiliary agents in the principal drug according to routine methods, which are for general use in the pharmaceutical preparation field, such as excipients, binders, disintegrators, lubricants, flavor, auxiliary dissolution agents, suspending agents, and coating agents.

In case that the caries-suppressing material is used as an oral composition (including an oral composition as a composition for preventing periodontal diseases), the caries-suppressing material of the invention is used as the essential component. Depending on the shape, various known ingredients may be blended. Known ingredients possibly in blend therein include for example moistening agents, thickeners, agents for reinforcing teeth, sterilizers, pH adjusters, surfactants, enzymes, anti-inflammatory agents, blood circulation-promoting agents, sweeteners, preservatives, colorants, dyes and flavor, which may appropriately be used.

The oral composition may be prepared by blending the caries-suppressing material of the invention according to routine methods and may be prepared into toothpaste, dental cream, tooth powder, dental liquid, oral pasta, mouthwash, tablets for gargling, tablets for washing artificial teeth, massage cream for gingiva, chewing gum, troche, and candies. Most appropriately, the oral composition is in the forms of dental liquids at low viscosity, mouthwash, mouthwash, tablets for gargling and washing agents of artificial teeth for use in dissolution in water. In accordance with the invention, the oral composition means a composition to be masticated or to be used for gargling and includes for example foods such as chewing gum, candies, confectionary tablets, and confectionary films; and quasi-pharmaceutical products such as toothpaste, dental liquid and mouthwash.

The term "cariogenic sugar" means a sugar as a nutritious source for bacteria causing caries to generate non-water-soluble glucan and organic acids, and includes sugars for example sucrose, fructose and glucose. Preferably, the oral composition never contains these cariogenic sugars but may contain non-cariogenic sugars for example sugar alcohols such as Xylitol, maltitol, erythritol, sorbitol, lactitol, reduced palatinose, and mannitol; reduced glutinous starch syrup or sweeteners at high sweetness levels, for example saccharin, sucralose, and Acesulfame K. Nonetheless, the caries-suppressing material of the invention may be used in combination with cariogenic sugars.

In case that the caries-suppressing material is used as an oral composition, ingredients generally blended in oral compositions may appropriately be blended within a range with no deterioration of the invention, depending on the dosage form, other than the ingredients described above. For example, polishing agents, moistening agents, thickeners, surfactants, flavor, sweeteners, colorants, preservatives, pH adjusters and various pharmaceutically active components may be blended within a range without any deterioration of the advantages of the invention.

Polishing agents include for example aluminium oxide, aluminum hydroxide, aluminium silicate, zirconium silicate, silicic anhydride, precipitating silica, silica gel, calcium carbonate, calcium pyrophosphate, calcium hydrogen phosphate, calcium phosphate, tricalcium phosphate, hydroxyapatite, fluoroapatite, halogenated apatite, magnesium carbonate, magnesium phosphate, insoluble sodium metaphosphate, titanium oxide, zeolite and synthetic resin-series polishing agents.

Moistening agents include sugar alcohols such as sorbitol, maltitol, Xylitol and lactitol, and polyhydric alcohols such as glycerin, 1,3-butylene glycol, 1,2-pentanediol, polyethylene glycol, polypropylene glycol and dipropylene glycol.

Thickeners include carboxyvinyl polymer, carboxymethylcellulose sodium, methylcellulose, hydroxyethylcellulose, carrageenan, alkali metal salts of aliginic acid such as sodium alginate, gums such as gellan gum, xanthan gum, guar gum, tragacanth gum, karaya gum, veegum, and gum Arabic, and polyvinyl alcohol, polyvinyl pyrrolidone, silica gel and aluminium silica gel.

Surfactants include anionic surfactants, cationic surfactants, amphoteric surfactants, and nonionic surfactants and specifically include alkyl sulfate salts, alkylbenzene sulfonate salts, sucrose fatty acid ester, lactose fatty acid ester, lauroylsarcosine salts, N-acylglutamate salts, α-olefinsulfonate salts, 2-alkyl-N-carboxy-N-hydroxyethylimidazolium betaine, N-acyl taurine salts, alkylol amide, polyoxyethylene sorbitan fatty acid ester, polyoxyethylene hardened castor oil or fatty acid esters thereof, polyglycerin fatty acid ester, sorbitan fatty acid ester, fatty acid ester, polyethylene glycol fatty acid ester, and propylene glycol fatty acid ester.

Flavor includes menthol, peppermint oil, spearmint oil, orange oil, lemon oil, eucalyptus oil, mint oil, acacia oil, anise oil, bitter almond oil, calamus oil, camphor oil, cinnamon oil, cinnamon bark oil, cinnamon leaf oil, rose oil, sandalwood oil, clove oil, herb oil, banana oil, apple oil, methyl salicylate, carbon, anethole, terpenes such as limonene and compound perfume.

Sweeteners include saccharin, sodium saccharin, Xylitol, stevioside, stevia extract, rebaudioside, p-methoxycinnamic aldehyde, neohesperidine dihydroxychalcone, perillartine, thaumatine, glycyrrhizin, glycyrrhizin monoglucoside, hernandulcin, trehalose, aspartame and sorbit.

Colorants include authorized dyes such as Blue No. 1 and Yellow No. 4, titanium dioxide and caramel.

Preservatives include p-oxybenzoate esters, benzoate salts, alkyldiaminoethyl glycine hydrochloride, and phenoxyethanol. pH adjusters include organic acids such as citric acid, malic acid, and acetic acid and salts thereof; sodium carbonate, sodium hydrogen carbonate, potassium carbonate, potassium hydrogen carbonate, calcium carbonate, calcium hydrogen carbonate, ammonium carbonate, ammonium hydrogen carbonate, sodium potassium carbonate, lithium carbonate, urea, amino acid oligomers, sodium chloride, inorganic calcium such as calcium chloride, calcium nitrate, calcium sulfate, calcium glycerophosphate, and calcium hydroxide, and organic acid calcium salts such as calcium lactate, calcium acetate, calcium malonate, calcium citrate, calcium glycolate, calcium glycerate, calcium tartrate, and calcium phytinate.

Pharmaceutically active Components include allantoin, tocopherol acetate, isopropylmethyl phenol, glycyrrhizinates, glycyrrhezinates, dextrase, chlorophyll, sodium copper chlorophyll, flavonoid, tranexamic acid, mutanase, lysozyme, amylase, protease, lytic enzymes, superoxide dismutase, ε-aminocaproic acid, aluminium allantoin, aluminium chlorohydroxyallantoin, dihydrocholestanol, bisabolol, glycerophosphate, water-soluble inorganic phosphate compounds, fluorides such as sodium fluoride, sodium monofluorophosphate, tin fluoride, potassium fluoride, sodium fluorosilicate, aluminium fluoride, silver fluoride, hexylamine hydrofluorate, decanolamine hydrofluorate, and octadecenylamine hydrofluorate, ethylenediaminetetraacetic acid, zinc citrate, zinc chloride, copper gluconate, chlorhexizine gluconate, copper chloride, polyphosphate salts, pyrophosphate salts, vitamins such as vitamins A, C, E, B6, and pantothenate salts, amino acids such as glycine, lysine and histidine, sodium chloride, sodium bicarbonate, aluminium lactate, potassium nitrate, sarcosinate, polyphenol compounds such as catechins, and crude drugs of plant and animal origins.

Additionally, ethanol, water, silicone substances, sugar alcohols and natural extracts can appropriately be blended. Herein, ethanol is preferably blended at an amount corresponding to 5 to 10% by weight.

The oral composition of the invention is blended together with the ingredients described above by routine methods, to be formulated into various dosage forms.

The type and ratio of the caries-suppressing material of the invention contained in the composition can appropriately be selected by persons skilled in the art, depending on the types and uses of the composition, the caries-suppressing material and other sweetness ingredients. Additionally, the caries-suppressing food composition in accordance with the invention may contain individual appropriate ingredients conventionally known in the technical art, and such caries-suppressing food composition may be prepared and produced by persons skilled in the art according to conventionally known methods.

As described above, the content of the rare sugar is not specifically limited but is generally contained at 0.1 to 99% in the composition to achieve the intended effect. Further, the composition of the invention may additionally contain one or two or more of Xylitol, maltitol, Palatinit, mannitol, sorbitol, palatinose, panose oligosaccharide, lactitol, erythritol, coupling sugar and isomalto-oligo, which are all considered to have non-cariogenicity.

The composition may also contain catechins and tea extracts, in addition to coffee, tea and black tea containing phenolic compounds.

In case that the composition is used as a pharmaceutical composition, the composition is used at an amount variable depending on the symptoms, the age, the body weight, the designing method and the dosage form. Generally, however, the composition is used as a raw material to give sweetness to sugar-coated tablets, gargle and toothpaste.

The invention is now described in detail in the following Examples. But the technical scope of the invention is never limited by these Examples. The bacterial strain for use in experiments was two strains JCM5075 and JCM5175 of *Streptococcus mutans* (*S. mutans*).

Reference Example

Formation of Insoluble Glucan with *S. mutans*

*S. mutans* strains characteristically form insoluble glucan on addition of sucrose, to reduce the pH of the culture medium, which is considered to cause decalcification of dental surface to form decayed teeth (the reason why the strains are designated bacteria causing decayed teeth). The *S. mutans* strain JCM5075 was plated in a Brain Heart Infusion (BHI) broth, for culturing under anaerobic conditions, to visually determine the bacterial growth (potency for forming insoluble glucan: optical density) with naked eyes.

When sucrose was added, JCM5075 formed insoluble glucan, which was deposited on the inner face of a glass tube to form bacterial masses. This is apparently observed with naked eyes (FIG. 1)

Figure 1:
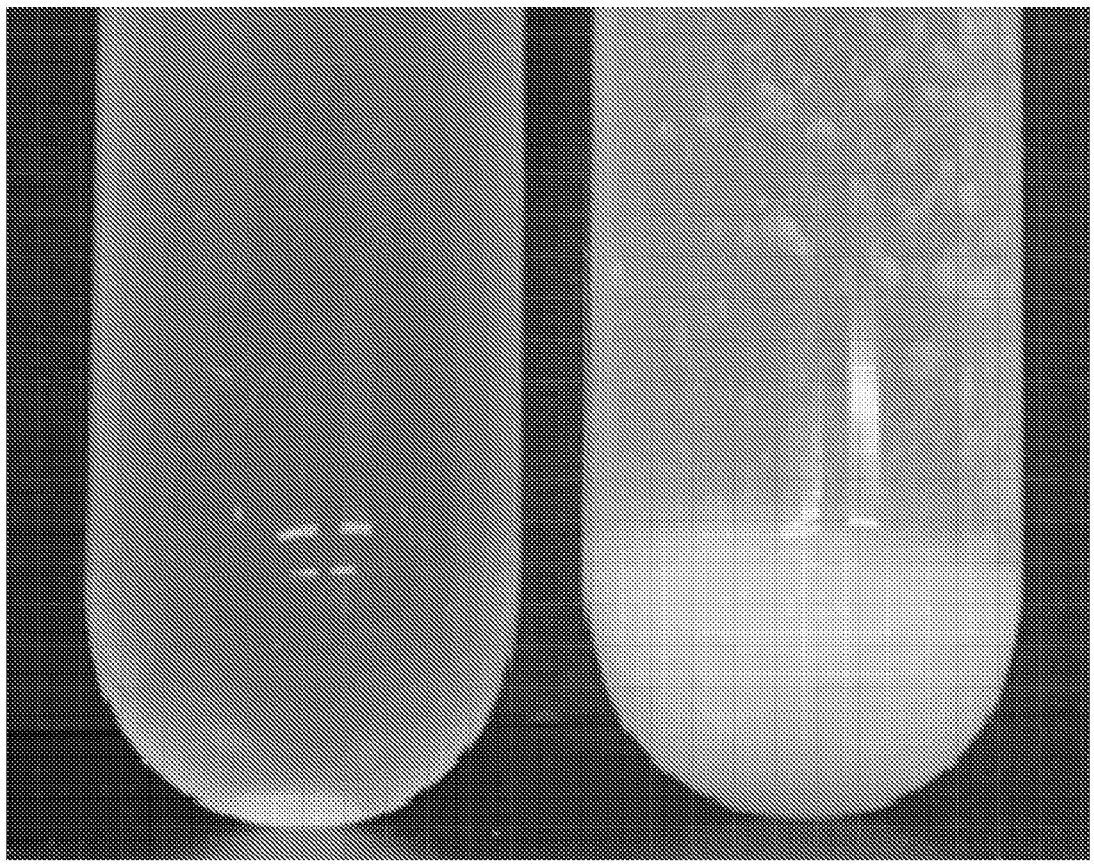
FIG. 1 A photograph in place of drawings describing that the strain *Streptococcus mutans* assimilated sucrose and formed insoluble glucan.

Based on the results in FIG. 1, it was verified that the *S. mutans* strain assimilated sucrose to form insoluble glucan.

Example 1

*S. mutans* strains characteristically form insoluble glucan on addition of sucrose, to generate acids and reduce the pH of the culture medium, which is considered to cause decalcification of teeth on dental surface to form decayed teeth (the reason why the strains are designated bacteria causing decayed teeth). JCM 5075 of *S. mutans* strains and the Brain Heart Infusion (BHI) broth were used to assay the optical density (the increase of the number of the bacterial cells) and the pH change in individual rare sugar solutions with or without sucrose added. As the rare sugars, there were used D-fructose, L-fructose, D-sorbose, L-sorbose, D-psicose, L-psicose, D-tagatose and L-tagatose. The rare sugars used were supplied from the Rare Sugar Research Center, the National University Corporation Kagawa University.

The strain JCM5075 thawed from −80° C. stock was cultured for 48 hours, and was adjusted to OD 0.3. 100 μl of the resulting culture was added to each 2-ml portion of the BHI broths under individual conditions, to assay the optical density and the pH 24 hours later (observation with naked eyes and absorbance: $OD_{600}$).

After culturing for a given period of time, the culture was observed with naked eyes; and the optical density of a part of the liquid culture was measured with an absorptiometer ($OD_{600}$). The results are shown in Table 1 and FIG. 2.

After collecting a part of the liquid culture and centrifuging the culture, the pH of the resulting supernatant was measured with a pH meter. The results are shown in Table 2 (0, 6, 8, 12 and 24 hours after the addition of the bacteria to the BHI broth) and FIG. 3.

TABLE 1

| Test substance | Optical density (OD) 12 hours later |
|---|---|
| No addition | 0.186 |
| 1% sucrose | 0.060 |
| 10% Xylitol | 0.046 |
| 10% D-fructose | 0.114 |
| 10% L-fructose | 0.037 |
| 10% D-sorbose | 0.102 |
| 10% L-sorbose | 0.463 |
| 10% D-psicose | 0.158 |
| 10% L-psicose | 0.067 |
| 10% D-tagatose | 0.132 |
| 10% L-tagatose | 0.026 |

TABLE 2

| | pH | | | | |
|---|---|---|---|---|---|
| Test substance | 0 hour later | 6 hours later | 8 hours later | 12 hours later | 24 hours later |
| No addition | 7.3 | 7.2 | 7.2 | 6.6 | 5.9 |
| 1% sucrose | 7.4 | 7.2 | 7.2 | 6.7 | 4.7 |
| 5% Xylitol | 7.3 | 7.2 | 7.2 | 7.2 | 6.4 |
| 5% Xylitol + 1% sucrose | 7.3 | 7.2 | 7.2 | 7.1 | 4.9 |
| 10% Xylitol | 7.4 | 7.2 | 7.2 | 7.2 | 6.5 |
| 10% Xylitol + 1% sucrose | 7.3 | 7.2 | 7.2 | 7.2 | 5.1 |
| 5% D-fructose | 7.4 | 7.2 | 7.2 | 7.2 | 4.7 |
| 5% D-fructose + 1% sucrose | 7.4 | 7.2 | 7.2 | 7.2 | 5.0 |
| 10% D-fructose | 7.3 | 7.2 | 7.2 | 7.2 | 6.5 |
| 10% D-fructose + 1% sucrose | 7.3 | 7.2 | 7.2 | 7.2 | 5.1 |
| 5% L-fructose | 7.4 | 7.2 | 7.2 | 7.2 | 4.7 |
| 5% L-fructose + 1% sucrose | 7.3 | 7.2 | 7.2 | 7.2 | 5.0 |
| 10% L-fructose | 7.3 | 7.2 | 7.2 | 7.2 | 6.5 |
| 10% L-fructose + 1% sucrose | 7.3 | 7.2 | 7.2 | 7.2 | 6.7 |
| 5% D-sorbose | 7.4 | 7.2 | 7.2 | 7.2 | 5.5 |
| 5% D-sorbose + 1% sucrose | 7.3 | 7.2 | 7.2 | 7.2 | 5.0 |
| 10% D-sorbose | 7.3 | 7.2 | 7.2 | 7.2 | 6.9 |
| 10% D-sorbose + 1% sucrose | 7.3 | 7.2 | 7.2 | 7.2 | 6.9 |
| 5% L-sorbose | 7.4 | 7.2 | 7.2 | 7.2 | 5.9 |
| 5% L-sorbose + 1% sucrose | 7.4 | 7.2 | 7.2 | 7.2 | 5.3 |
| 10% L-sorbose | 7.3 | 7.2 | 7.2 | 7.2 | 7.1 |
| 10% L-sorbose + 1% sucrose | 7.3 | 7.2 | 7.2 | 7.2 | 6.4 |
| 5% D-psicose | 7.4 | 7.3 | 7.2 | 7.2 | 7.0 |
| 5% D-psicose + 1% sucrose | 7.4 | 7.3 | 7.2 | 7.2 | 6.4 |
| 10% D-psicose | 7.3 | 7.2 | 7.2 | 7.2 | 7.2 |
| 10% D-psicose + 1% sucrose | 7.3 | 7.2 | 7.2 | 7.2 | 7.1 |
| 5% L-psicose | 7.3 | 7.2 | 7.2 | 7.2 | 6.8 |
| 5% L-psicose + 1% sucrose | 7.3 | 7.2 | 7.2 | 7.2 | 6.2 |
| 10% L-psicose | 7.2 | 7.1 | 7.0 | 7.0 | 6.9 |
| 10% L-psicose + 1% sucrose | 7.2 | 7.1 | 7.0 | 7.0 | 6.9 |
| 5% D-tagatose | 7.3 | 7.2 | 7.2 | 7.2 | 7.0 |
| 5% D-tagatose + 1% sucrose | 7.3 | 7.2 | 7.2 | 7.2 | 6.9 |
| 10% D-tagatose | 7.1 | 7.0 | 7.0 | 7.0 | 6.9 |
| 10% D-tagatose + 1% sucrose | 7.1 | 7.0 | 7.0 | 7.0 | 6.9 |
| 5% L-tagatose | 7.3 | 7.2 | 7.2 | 7.2 | 6.6 |
| 5% L-tagatose + 1% sucrose | 7.3 | 7.2 | 7.2 | 7.2 | 6.0 |
| 10% L-tagatose | 7.1 | 7.0 | 6.9 | 6.9 | 6.8 |
| 10% L-tagatose + 1% sucrose | 7.1 | 7.0 | 6.9 | 6.9 | 6.8 |

No difference in optical density and pH change was observed between 6 and 8 hours later, but a difference therein was observed between 12 and 24 hours later.

Figure 2:
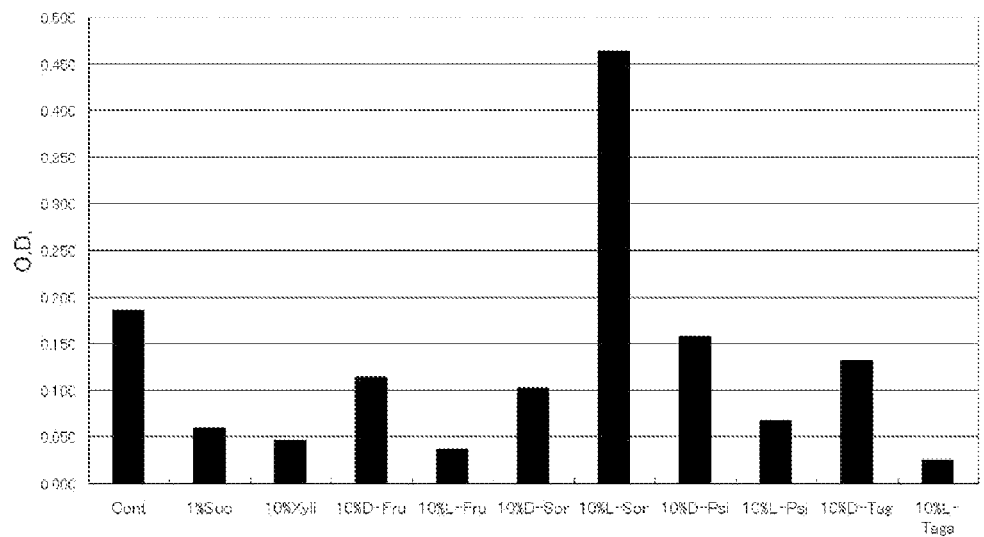
FIG. 2 Bar graphs depicting the change of the optical density ($OD_{600}$) of the solutions of rare sugars 24 hours later, where JCM5075 (a strain of *Streptococcus mutans*) and the BHI broth were used. The optical density was compared between culturing with no sucrose addition and culturing with sucrose addition.

FIG. 2 shows the change of the optical density 24 hours later. As in FIG. 1, those with addition of 1% sucrose and with addition of 10% D-fructose caused the precipitation of bacterial masses (insoluble glucan) under observation with naked eyes. Therefore, the reduction of the optical density was observed.

With no addition (the BHI broth), no formation of any precipitate (insoluble glucan) was observed under naked eyes, so it was considered that comparison based on OD could be done. Compared with no addition, the suppression of OD increase was observed with D-psicose, D-sorbose, D-tagatose, L-fructose, L-psicose, and L-tagatose as other sugars. It is noted in particular that the suppressive effect of L-tagatose was high. Then, the effect was high in the decreasing order of L-fructose, Xylitol, L-psicose and D-sorbose.

Figure 3:
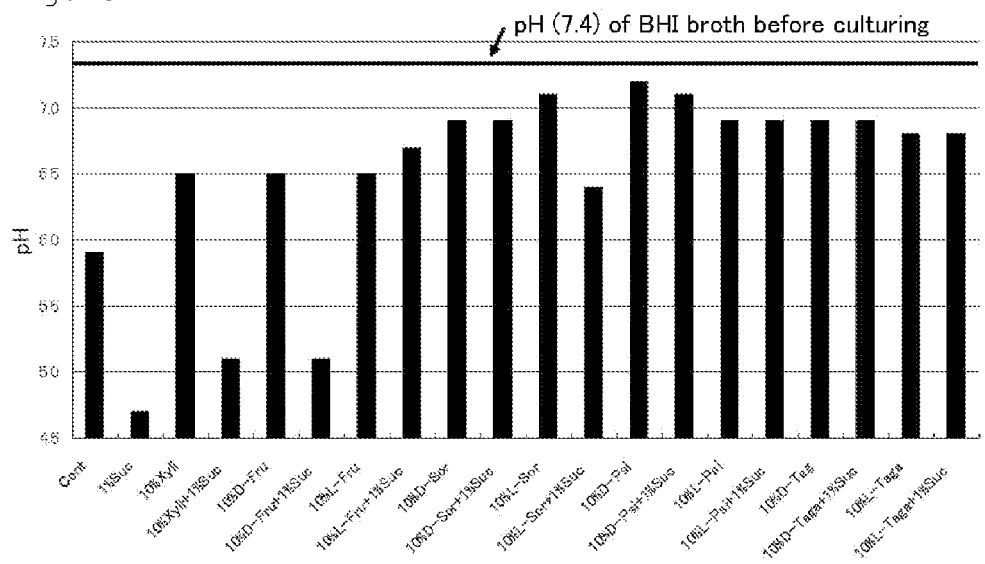
FIG. 3 Bar graphs depicting the change of the pH of the solutions of rare sugars 24 hours later, where JCM5075 (a strain of *Streptococcus mutans*) and BHI solution were used. pH changes were compared between no sucrose addition and sucrose addition. Additionally, the interactions between individual rare sugars and sucrose are also shown.

FIG. 3 shows the pH change 24 hours later. The pH was highly inclined to acidity with 1% sucrose, or 10% Xylitol+1% sucrose, or 10% fructose+1% sucrose, which may indicate that acids were generated. Alternatively, other sugars exerting the suppression of the growth in FIG. 2 virtually involved the suppression of the pH reduction. Although D-psicose most highly suppressed the pH reduction, the effect thereof on the suppression of the bacterial growth was not so high. Possibly, D-psicose may have a different effect.

The pH reduction was suppressed with D-sorbose, D-tagatose, L-fructose, L-psicose and L-tagatose. No pH reduction even with 1% sucrose addition in particular strongly suggests the presence of cariostatic action. When 1% sucrose was added to Xylitol, the resulting mixture reduced the pH. This means that these sugars suppress the growth of S. mutans and the potency thereof to generate acids, so a caries-suppressing effect may be expected for these sugars.

As described above, the effect against S. mutans could be verified through the measurement with naked eyes and the change of absorbance (OD) and pH.

Example 2

Actions of D- and L-Psicose Against S. mutans

D-Psicose and L-psicose were used to assay the actions thereof against S. mutans. D-Psicose and L-psicose were supplied from the Rare Sugar Research Center, the National University Corporation Kagawa University. The S. mutans strain MT 8148 (JCM5175) was plated in a Brain Heart Infusion broth supplemented with agar for culturing at 37° C. for 48 hours. The liquid culture was inoculated in a fresh Brain Heart Infusion broth, for culturing at 37° C. for 24 hours. The liquid culture was inoculated in a phenol red broth (PRB broth) containing a test substance at 1%, for culturing at 37° C.; the bacterial growth (absorbance at 660 nm: OD) and the pH were assayed 48 hours later. As a control, glucose, fructose, sucrose and Xylitol were used. The results are shown in Table 3. After culturing for a given period of time, additionally, the optical density of apart of the liquid culture was measured with an absorptiometer (OD 660 nm).

TABLE 3

| Test substance | pH | OD |
| --- | --- | --- |
| No addition | 5.9 | 0.03 |
| Sucrose | 3.9 | 0.14 |
| D-Glucose | 3.9 | 0.26 |
| L-Fructose | 4.0 | 0.20 |
| Xylitol | 6.1 | 0.03 |
| D-Psicose | 5.9 | 0.02 |
| L-Psicose | 5.9 | 0.02 |

The results in Table 3 show that as the consequence of the culturing of S. mutans in the culture medium supplemented with D- or L-psicose, glucose, fructose, sucrose and Xylitol, the bacterial growth with addition of D- or L-psicose and Xylitol was represented by $OD_{660}$, which was 0.05 or less, while the liquid culture was at pH 5.5 or more. Compared with OD=0.26 and pH 3.9 in the liquid culture with glucose addition, a significant difference was observed. Thus, it is assumed that the substances have an excellent caries-suppressing action.

Example 3

Action of Allitol and D-Sorbose Against S. mutans

Allitol and D-sorbose were used to assay the actions thereof against S. mutans. Allitol and D-sorbose were supplied from the Rare Sugar Research Center, the National University Corporation Kagawa University. The S. mutans strain (JCM5075) was plated in a Brain Heart Infusion broth containing a 10% test substance, to measure the pH of the liquid culture after 48-hour culturing. As a control, 1% sucrose and 10% Xylitol were used. The results are shown in Table 4.

TABLE 4

| Test substance | pH |
| --- | --- |
| No addition | 5.5 |
| Sucrose | 4.0 |
| Xylitol | 6.0 |
| Allitol | 5.6 |
| D-sorbose | 5.0 |

As in the case of Example 2, the results in Table 4 show that allitol exerted an excellent non-cariogenic property at pH 5.5 or more. Additionally, it is shown that D-sorbose is at a low assimilability with the S. mutans strain.

Example 4

Cariostatic Test with D-Psicose

A cariostatic test with D-psicose was carried out. Additionally, the effect of catechins added was also examined. D-Psicose was supplied from the Rare Sugar Research Center, the National University Corporation Kagawa University. As the catechin, Polyphenon 70A of Mitsui Norin Co., Ltd. was used. The S. mutans strain MT 8148 (JCM5175) was plated in a Brain Heart Infusion broth supplemented with agar, for culturing at 37° C. for 48 hours. Further, the resulting liquid culture was inoculated in a fresh Brain Heart Infusion broth, for culturing at 37° C. for 24 hours. The liquid preculture was inoculated in a phenol red broth (PRB broth) containing sugars and catechins at the following concentrations for culturing at 37° C.; 20 hours later, the pH was measured. As a control, sucrose was used. The results are shown in Table 5.

TABLE 5

| Test substance | pH |
| --- | --- |
| No addition | 6.1 |
| 0.25% Sucrose | 4.5 |
| 0.25% Sucrose + 3.3% D-psicose | 4.4 |
| 0.25% Sucrose + 5.0% D-psicose | 5.5 |
| 33 ppm catechin | 6.1 |
| 0.25% Sucrose + 33 ppm catechin | 4.4 |
| 0.25% Sucrose + 17 ppm catechin + 2.5% D-psicose | 5.4 |

The results in Table 5 show that D-psicose as a rare sugar at a concentration of 5% exerted an action of suppressing the pH reduction in a culture medium with addition of sucrose, where S. mutans was cultured. Therefore, it was possibly indicated that D-psicose had an excellent cariostatic property. Although it was observed that catechin alone and D-psicose alone could not exert their pH-reducing actions at their individual concentrations, the co-existence of D-psicose at the concentrations with a trace amount of catechin suppressed the pH-reducing action. Hence, it is assumed that D-psicose and catechin exert a cariostatic action via their synergistic actions.

Example 5

An oral composition using a rare sugar with the cariostatic action in accordance with the invention was prepared on the basis of the composition table in Table 6 (toothpaste).

TABLE 6

| Toothpaste | |
| --- | --- |
| Ingredient | Ratio (%) |
| Calcium carbonate | 30.0 |
| Sodium fluoride | 0.2 |
| Carboxymethyl cellulose Na | 1.5 |
| Citric acid | 2.0 |
| Lauryl sulfate Na | 1.5 |
| Menthol | 0.6 |
| D-Psicose | 20.0 |
| Glycerin | 30.0 |
| Green tea extract | 1.0 |
| pH adjuster | Appropriate amount |
| Water | Appropriate amount |

Example 6

A mouthwash composition using a rare sugar with the cariostatic action in accordance with the invention was prepared on the basis of the composition table in Table 7 (mouthwash).

TABLE 7

| Mouthwash | |
| --- | --- |
| Ingredient | Ratio (%) |
| Ethanol | 20.0 |
| Sodium fluoride | 0.1 |
| Emanon CH-40 | 1.5 |
| Citric acid | 2.0 |
| Lauryl sulfate Na | 0.5 |
| Menthol | 0.2 |
| Glycerin | 15.0 |
| D-Psicose | 20.0 |
| Green tea extract | 1.0 |
| pH adjuster | Appropriate amount |
| Water | Appropriate amount |

Example 7

A chewing gum using a rare sugar with the cariostatic action in accordance with the invention was prepared on the basis of the composition table in Table 8 (chewing gum).

TABLE 8

| Chewing gum | |
| --- | --- |
| Ingredient | Ratio (%) |
| Gum base 1 | 13.5 |
| Gum base 2 | 13.5 |
| Glycerin | 1.5 |
| Citric acid | 1.5 |
| Lemon flavor | 1.2 |
| Green tea extract | 1.0 |
| Yellow dye from safflower | 0.1 |
| D-Psicose | 40.0 |
| pH adjuster | Appropriate amount |
| Water | Appropriate amount |

Using D-psicose in the compositions of the toothpaste, the mouthwash, and the chewing gum in the compositions in Examples through 7, the resulting toothpaste, mouthwash and chewing gum with refreshing sweetness without inducing caries could be prepared.

Herein, existing pharmaceutical ingredients, such as cetylpyridinium chloride, triclosan, cineole, thymol, zinc chloride, methyl salicylate and vitamin E can be added to the toothpaste and the mouthwash composition. Additionally, sugar alcohols with a cariostatic action such as Xylitol can be added to the chewing gum.

INDUSTRIAL APPLICABILITY

The metabolic level of D-psicose itself with a bacterium causing caries, namely S. mutans is low or is hardly observed (non-cariogenicity). Using D-psicose in combination with existing sweeteners, D-psicose exerts an action substantially suppressing bacterial growth and pH reduction with the cariogenic sweetness ingredients therein (cariostatic property) and therefore, D-psicose is widely applicable to for example foods, quasi-pharmaceutical products and pharmaceutical products.

In particular, Xylitol as a sugar alcohol belonging to one group of rare sugars is added to favorite foods and foods for use in daily life, and it is generally known widely that Xylitol exerts a high effect on the prevention of caries. The other rare sugars in accordance with the invention may have an effect as an anticarious sweetener, so these rare sugars would possibly be new "anticarious sweeteners developed in Japan" in place of Xylitol.

It is expected that identical toothpaste, mouthwash and chewing gum would be prepared from D-sorbose, D-tagatose, L-fructose, L-psicose, L-tagatose or allitol, other than D-psicose.

What is claimed is:

1. A method for suppressing a formation of insoluble glucan and acids which is caused due to caries-inducing oral bacteria, the method comprising:
    administering a composition comprising D-psicose and catechins which comprise epigallocatechin or epigallocatechin gallate to a subject in need of the suppression of the formation of insoluble glucan and acids.

* * * * *